(12) United States Patent
Janssen et al.

(10) Patent No.: US 8,223,337 B2
(45) Date of Patent: Jul. 17, 2012

(54) APPARATUS, SYSTEM, AND METHOD FOR AFTERTREATMENT CONTROL AND DIAGNOSTICS

(75) Inventors: John M. Janssen, Henrico, VA (US); Frederick H. Lindner, Aesch (CH); Matthew L. Schneider, Seymour, IN (US)

(73) Assignee: Cummins Inc., Columbus, IN (US)

(*) Notice: Subject to any disclaimer, the term of this patent is extended or adjusted under 35 U.S.C. 154(b) by 43 days.

(21) Appl. No.: 12/610,830

(22) Filed: Nov. 2, 2009

(65) Prior Publication Data
US 2011/0170102 A1  Jul. 14, 2011

Related U.S. Application Data

(60) Provisional application No. 61/197,897, filed on Oct. 31, 2008, provisional application No. 61/197,898, filed on Oct. 31, 2008.

(51) Int. Cl.
*G01N 21/00* (2006.01)
(52) U.S. Cl. ...................................................... 356/438
(58) Field of Classification Search .................. 356/432, 356/438
See application file for complete search history.

(56) References Cited

U.S. PATENT DOCUMENTS

| | | | |
|---|---|---|---|
| 4,578,762 A | 3/1986 | Wong | |
| 4,694,173 A | 9/1987 | Wong | |
| 4,756,622 A | 7/1988 | Wong | |
| 4,795,240 A | 1/1989 | Wong et al. | |
| 4,850,697 A | 7/1989 | Schoennauer et al. | |
| 4,924,095 A | 5/1990 | Swanson, Jr. | |
| 5,241,367 A * | 8/1993 | Grob et al. | 356/435 |
| 5,464,982 A | 11/1995 | Drucker et al. | |
| 5,464,983 A | 11/1995 | Wang | |
| 5,583,339 A | 12/1996 | Black et al. | |
| 5,617,720 A * | 4/1997 | Achleitner et al. | 60/274 |
| 5,767,776 A | 6/1998 | Wong | |
| 5,798,700 A | 8/1998 | Wong | |
| 5,834,777 A | 11/1998 | Wong | |
| 5,889,199 A | 3/1999 | Wong et al. | |
| 5,894,373 A | 4/1999 | Wong | |
| 5,945,924 A | 8/1999 | Marman et al. | |
| 5,966,077 A | 10/1999 | Wong | |
| 6,029,442 A | 2/2000 | Caren et al. | |
| 6,047,543 A | 4/2000 | Caren et al. | |
| 6,048,500 A | 4/2000 | Caren et al. | |
| 6,107,925 A | 8/2000 | Wong | |
| 6,166,647 A | 12/2000 | Wong | |
| 6,237,575 B1 | 5/2001 | Lampert et al. | |
| 6,253,544 B1 | 7/2001 | Miller et al. | |
| 6,264,899 B1 | 7/2001 | Caren et al. | |
| 6,321,531 B1 | 11/2001 | Caren et al. | |
| 6,330,794 B1 | 12/2001 | Caren et al. | |
| 6,344,798 B1 | 2/2002 | Schell | |
| 6,357,223 B1 | 3/2002 | Caren et al. | |

(Continued)

*Primary Examiner* — Roy M Punnoose
(74) *Attorney, Agent, or Firm* — Matthew Fair; Krieg DeVault LLP

(57) ABSTRACT

A method includes providing an exhaust stream for an internal combustion engine, where the exhaust stream is fluidly coupled to an aftertreatment component. The method includes optically determining an amount of an exhaust gas constituent in the exhaust stream. The method further includes modifying a model stored on a computer readable medium in response to the amount of the exhaust gas constituent. The model is an engine $NO_x$ generation model, a catalyst $NO_x$ storage model, a catalyst $NO_x$ conversion model, a catalyst NO to $NO_2$ conversion model, a catalyst conversion efficiency model, an engine soot generation model, and/or a urea hydrolysis model.

12 Claims, 14 Drawing Sheets

U.S. PATENT DOCUMENTS

| | | |
|---|---|---|
| 6,810,660 B2 | 11/2004 | Hepburn et al. |
| 6,810,718 B2 | 11/2004 | Wilson et al. |
| 6,842,243 B2 | 1/2005 | Tokhtuev et al. |
| 6,917,038 B2 | 7/2005 | Zheng et al. |
| 6,982,431 B2 | 1/2006 | Modlin et al. |
| 7,084,963 B2 * | 8/2006 | Leipertz .......................... 356/73 |
| 7,176,460 B1 | 2/2007 | Wong |
| 7,178,331 B2 * | 2/2007 | Blakeman et al. ............... 60/301 |
| 7,186,979 B1 | 3/2007 | Wong |
| 7,202,948 B2 | 4/2007 | Buckley et al. |
| 7,214,939 B1 | 5/2007 | Wong |
| 7,240,482 B2 | 7/2007 | Hepburn et al. |
| 7,264,785 B2 * | 9/2007 | Blakeman et al. ......... 423/213.2 |
| 7,313,911 B2 * | 1/2008 | Pfeifer et al. .................... 60/286 |
| 7,409,823 B2 * | 8/2008 | Price et al. ....................... 60/307 |
| 7,480,044 B2 * | 1/2009 | Leipertz ......................... 356/301 |
| 2004/0237505 A1 * | 12/2004 | Leipertz .......................... 60/274 |
| 2005/0076655 A1 | 4/2005 | Wong |
| 2006/0251548 A1 * | 11/2006 | Willey et al. ................... 422/180 |
| 2006/0256330 A1 * | 11/2006 | Leipertz ......................... 356/301 |
| 2007/0029487 A1 | 2/2007 | Wong et al. |
| 2007/0029488 A1 | 2/2007 | Wong |
| 2008/0295499 A1 * | 12/2008 | Driscoll et al. ................. 60/288 |
| 2009/0193794 A1 * | 8/2009 | Robel et al. ..................... 60/295 |
| 2010/0083636 A1 * | 4/2010 | Wang et al. ..................... 60/277 |
| 2010/0101213 A1 * | 4/2010 | Tuomivaara et al. ........... 60/276 |

* cited by examiner

APPARATUS, SYSTEM, AND METHOD FOR AFTERTREATMENT CONTROL AND DIAGNOSTICS

RELATED APPLICATION

This application is related to, and claims the benefit of, U.S. Provisional Patent Application No. 61/197,897 entitled "Apparatus, system, and method for detecting engine fluid constituents" and U.S. Provisional Patent Application No. 61/197,898 entitled "Optical sensing in an adverse environment," both filed on Oct. 31, 2008 and both incorporated herein by reference.

BACKGROUND

Reliably monitoring exhaust gas constituents related to aftertreatment systems for internal combustion engines presents several challenges. Frequently, exhaust environments operate at very high temperatures that preclude use of many standard sensor types. Further, engine combustion constituents typically include soot and unburned hydrocarbons that can hamper operation of various sensing technologies. Present sensing technologies cannot detect various constituents of the exhaust gas and survive the exhaust environment. Various aftertreatment systems and technologies for internal combustion engines experience wear, failure, and operational variability that affect the final emissions of the engine-aftertreatment system. Presently available sensing technologies have very limited feedback for aftertreatment systems, making control and diagnostics for aftertreatment systems difficult. Thus, there is an ongoing demand for further contributions in this area.

SUMMARY

One embodiment is a unique method for determining an aftertreatment component performance in response to an optically determined exhaust gas constituent amount, and modifying and engine operating parameter in response to the aftertreatment component performance. Further embodiments, forms, objects, features, advantages, aspects, and benefits shall become apparent from the following description and drawings.

DESCRIPTION OF THE ILLUSTRATIVE EMBODIMENTS

Figure 1:
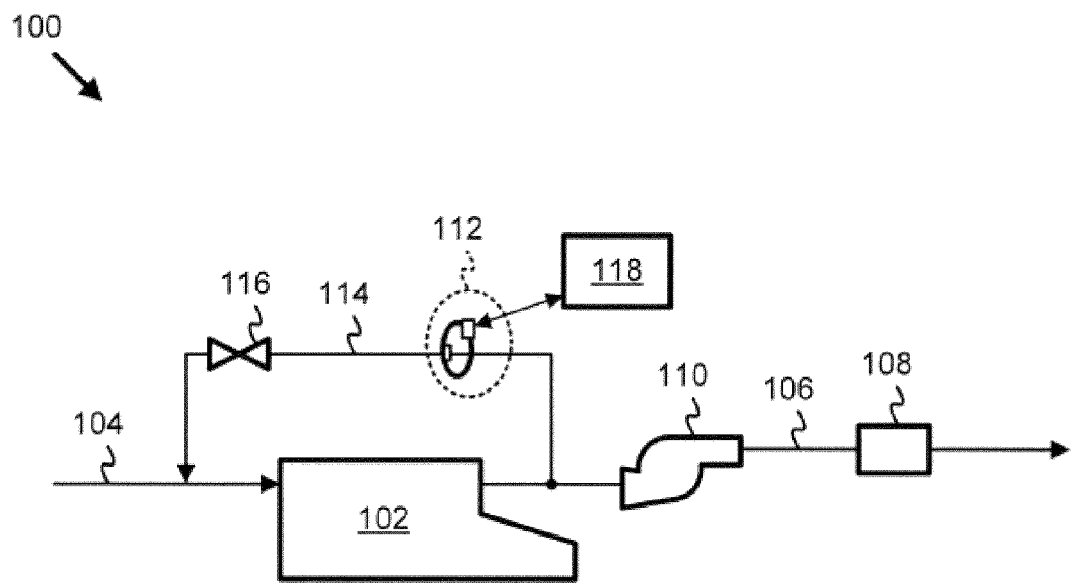
FIG. 1 is a schematic diagram of a system for detecting engine fluid constituents.

For the purposes of promoting an understanding of the principles of the invention, reference will now be made to the embodiments illustrated in the drawings and specific language will be used to describe the same. It will nevertheless be understood that no limitation of the scope of the invention is thereby intended, any alterations and further modifications in the illustrated embodiments, and any further applications of the principles of the invention as illustrated therein as would normally occur to one skilled in the art to which the invention relates are contemplated and protected.

Figure 10:
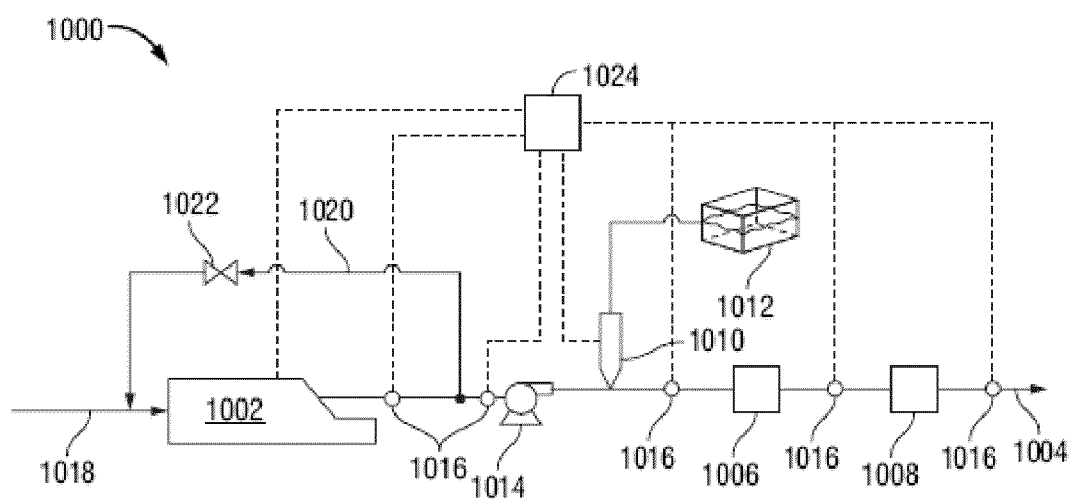
FIG. 10 is a schematic diagram of a system for determining a component performance and adjusting an engine operating parameter.

FIG. 10 is a schematic diagram of a system 1000 for determining a component performance and adjusting an engine operating parameter. The system includes an internal combustion engine 1002 producing an exhaust stream 1004 and having aftertreatment components 1006, 1008. The exemplary system 1000 includes a turbocharger 1014 and an exhaust gas recirculation (EGR) stream 1020 with an EGR valve 1022 that controls a flow rate of EGR. The system 1000 includes an intake stream 1018 for the internal combustion engine 1002. The system includes an injector 1010 that injects a reductant and/or reagent into the exhaust stream 1004, and a reductant (or reagent) storage vessel 1012. The storage vessel 1012 may be a urea storage vessel, a fuel tank of a vehicle wherein the internal combustion engine 1002 is installed, or any other vessel having a reductant (or reagent) known in the art.

The system 1000 includes a component performance controller 1024 in communication with one or more optical sensors 1016 to determine an amount of an exhaust gas constituent. Optical sensors 1016, as used herein, indicate any sensor utilizing electromagnetic waves in the infrared, visible, and ultraviolet frequency ranges of electromagnetic radiation. The placement of optical sensors 1016 is exemplary, and an optical sensor 1016 may be positioned anywhere within the system wherein an exhaust gas constituent determination is to be made. The amount of the exhaust gas constituent may be described as a fraction, percentage, concentration, or absolute mass of the constituent as understood in the art. The component performance controller 1024 may be in communication with any component of the system, and may further be an aftertreatment controller and/or the engine controller. The component performance controller 1024 may be a single controller, a plurality of distributed controllers, and may have certain functionality implemented in hardware, software, or both.

Figure 11:
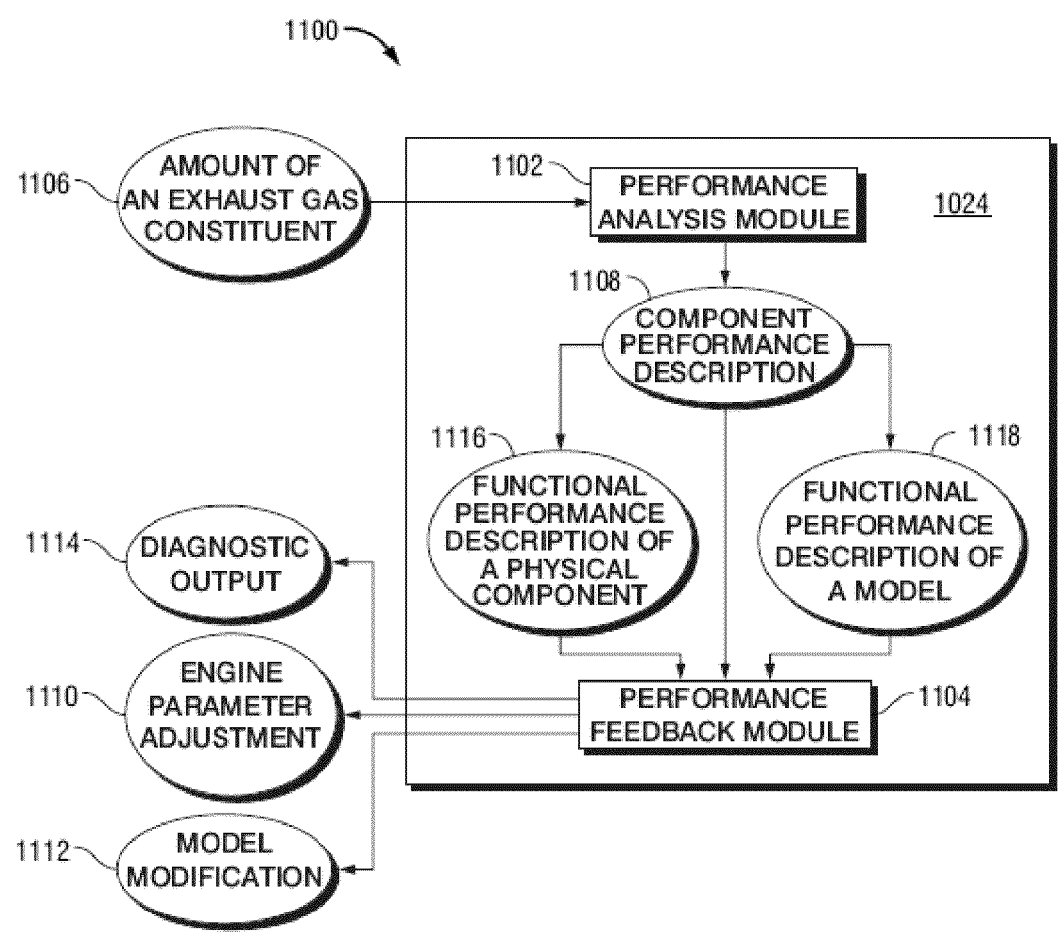
FIG. 11 is a schematic diagram of a component performance controller.

FIG. 11 is a schematic diagram of an apparatus 1100 including a component performance controller 1024. The apparatus 1100 a performance analysis module 1102 that determines a component performance description 1108 in response to an amount of the exhaust gas constituent 1106 determined with an optical sensor 1016. The performance feedback module 1104 provides an engine parameter adjustment 1110 in response to the component performance description 1108. In certain embodiments, the component performance description 1108 is a functional performance description of a physical component 1116. For example, the physical component may be a $NO_x$ adsorption catalyst, a $NO_x$ conversion catalyst, an $NO$—$NO_2$ conversion catalyst, an oxidation catalyst, a soot filter, and/or a reductant injector. Non-limiting examples of the functional performance description of the physical component 1116 include a catalyst conversion efficiency value, a catalyst storage capacity value, a filter integrity value, and/or an injection compliance value.

In certain embodiments, the component performance description 1108 is a functional performance description of a model 1118, and the performance feedback module 1104 adjusts an engine operating parameter by providing a model modification 1112. Non-limiting examples of a model include an engine-out soot model, an engine-out $NO_x$ model, an engine-out $NO_x$ composition model, a $NO_x$ adsorption model, a $NO_x$ release model, a $NO_x$ conversion model, a hydrocarbon oxidation model, an ammonia slip model, an unburned hydrocarbon slip model, an ammonia:$NO_x$ ratio model, and/or a urea hydrolysis model.

An exemplary embodiment includes the amount of the exhaust gas constituent 1106 as an amount of ammonia and an amount of $NO_x$, the component performance description 1108 as an ammonia:$NO_x$ ratio, and the engine parameter adjustment 1110 as a urea injection rate.

Another exemplary embodiment includes the performance analysis module 1102 determining the amount of the exhaust gas constituent 1106, determining the component performance description 1108 as a functionality of an aftertreatment component in response to the amount of the exhaust gas constituent 1106, and the performance feedback module 1104 providing a diagnostic output 1114 in response to the component performance description 1108. The diagnostic output 1114 can be any value indicating the compliance or non-compliance of an aftertreatment component, and may be used by an engine controller to set a malfunction indicator lamp (either ON or OFF), to set a maintenance lamp, to adjust engine controls, to store or clear a fault value, to increment or decrement a fault counter, to trigger additional fault checking or testing, and/or for any other purpose understood in the art.

Figure 12:
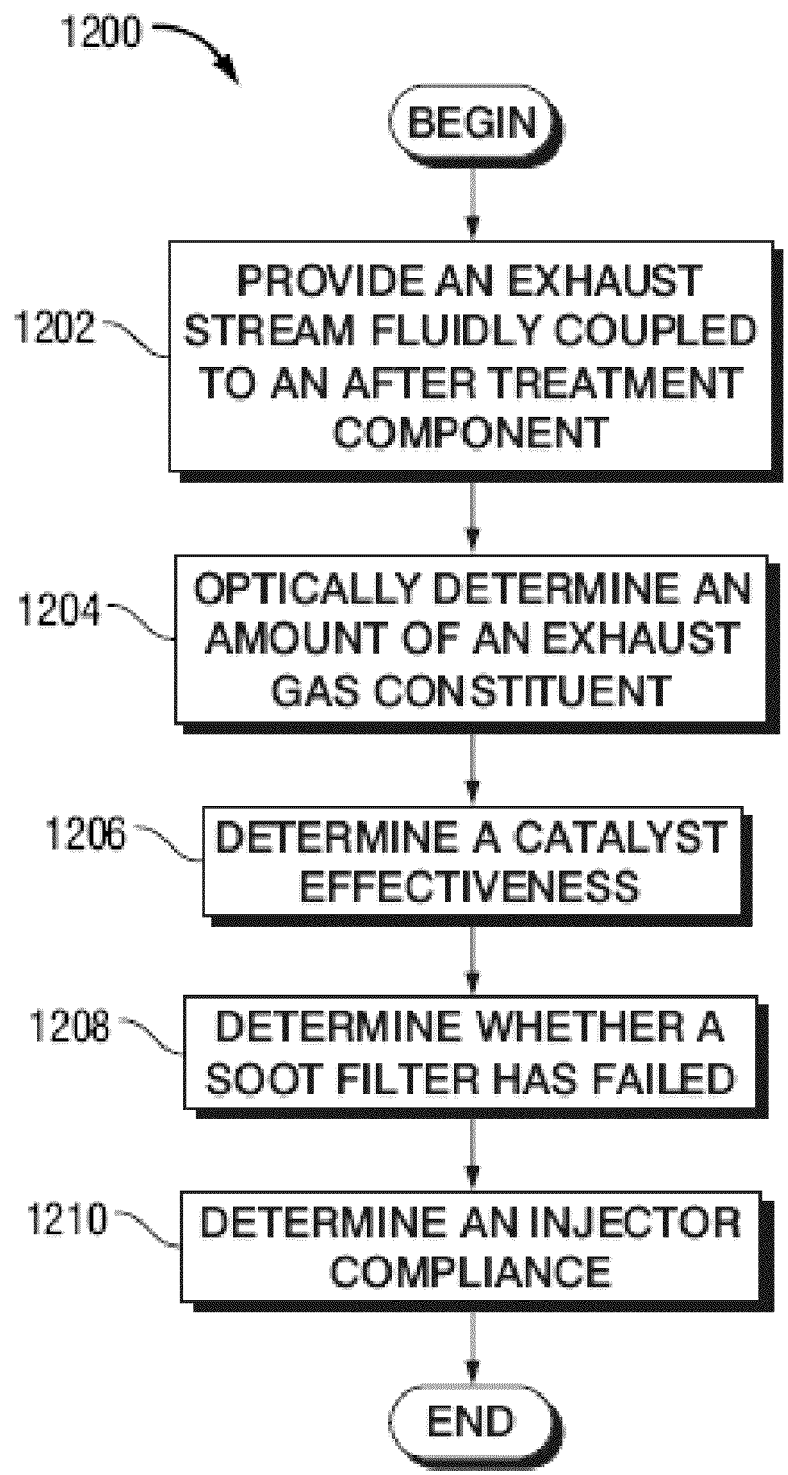
FIG. 12 is a schematic flow diagram of a technique for diagnosing a component.

FIG. 12 is a schematic flow diagram of a technique 1200 for diagnosing a component. The technique 1200 includes an operation 1202 to provide an exhaust stream for an internal combustion engine, the exhaust stream fluidly coupled to an aftertreatment component. The technique 1200 further includes an operation 1204 to optically determine an amount of an exhaust gas constituent in the exhaust stream, and an operation to diagnose an aftertreatment component in response to the amount of the exhaust gas constituent.

Various non-limiting examples of diagnosing an aftertreatment component in response to the amount of the exhaust gas constituent are described herein. One example is an operation 1206 to determine a catalyst effectiveness in response to the amount of the exhaust gas constituent. The catalyst effectiveness may be a catalyst adsorption effectiveness, a catalyst storage amount, and/or catalyst conversion effectiveness. The catalyst may be an oxidation catalyst, a $NO_x$ adsorption catalyst, a $NO_x$ conversion catalyst (e.g. lean $NO_x$ or selective catalytic reduction), an $NO$—$NO_2$ conversion catalyst (a type of oxidation catalyst), or a catalyzed soot filter.

Another example is an operation 1208 to determine whether a soot filter has failed. In one example, the operation 1208 includes determining a soot amount and size downstream of a soot filter, and determining the soot filter has failed if a soot amount or size exceeds a threshold value. In certain embodiments, the operation 1208 includes determining a source of the soot in response to the size of the soot, for example determining whether the soot is normal soot indicating a normal combustion operation, or abnormally sized soot consistent with an exhaust gas recirculation failure, a combustion event failure, a fuel injector failure, an injector 1010 failure where the injector places unburned hydrocarbons in the exhaust stream 1004, and/or a failure of an oxidation catalyst 1006. One of skill in the art can simulate the failures that are to be detected and determine the associated soot size profile as a matter of straightforward data collection.

Another example is an operation 1210 to determine an injector compliance. The injector may inject a reductant or a reagent, and the technique 1200 includes the operation 1210 to determine whether the injector is injecting the scheduled amount, is injecting with an appropriate response time, and/or is injecting with an appropriate geometric distribution in the exhaust stream. In a further embodiment, the technique 1200 includes determining whether the composition of the injected material, e.g. urea, is compliant with expectations, regulations, and/or the system design. For example, the technique 1200 can be utilized to determine whether a reductant vessel has been filled with water rather than urea.

Figure 15:
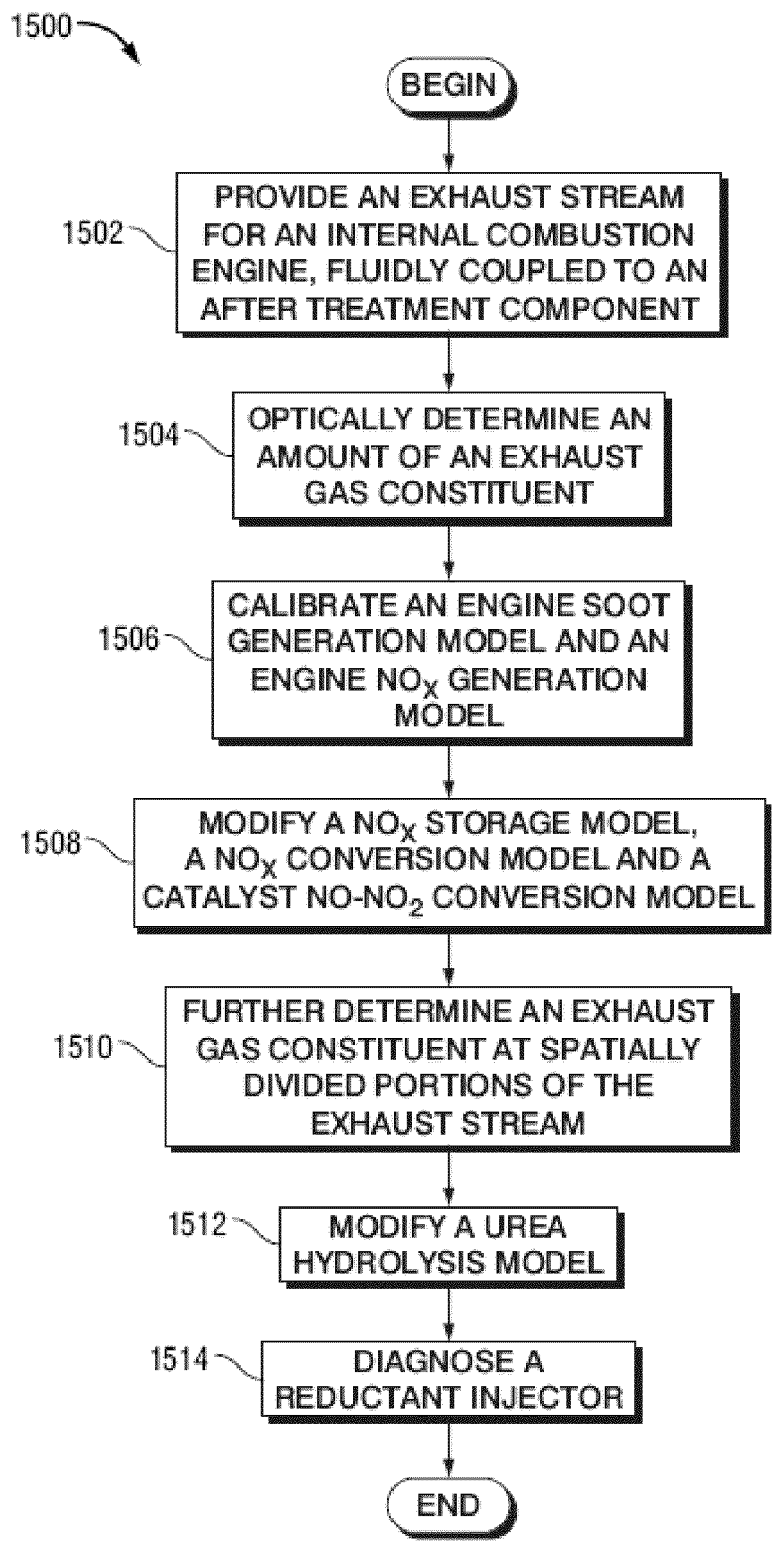
FIG. 15 is a schematic flow diagram of a technique for modifying a model in response to an amount of an exhaust gas constituent.

FIG. 15 is a schematic flow diagram of a technique 1500 for modifying a model in response to an amount of an exhaust gas constituent. The technique 1500 includes an operation 1502 to provide an exhaust stream for an internal combustion engine, where the exhaust stream is fluidly coupled to an aftertreatment component. The technique 1500 further includes an operation 1504 to optically determine an amount of an exhaust gas constituent in the exhaust stream, and an operation to modify a model stored on a computer readable medium in response to the amount of the exhaust gas constituent.

Various exemplary and non-limiting operations to modify a model in response to the amount of the exhaust gas constituent are described herein. The modification to the model can include calibrating a modeling parameter, resetting a modeling parameter, and/or resetting an integrator within the model. A modification operation includes the operation 1504 determining an amount of soot and/or $NO_x$ in the exhaust stream, and an operation 1506 to calibrate an engine soot generation and/or an engine $NO_x$ generation model in response to the determined amount of soot and/or $NO_x$. The operation 1504 to determine the amount of $NO_x$ may include determining an amount of NO and an amount of $NO_2$, where the engine $NO_x$ generation model may include modeling the amount of NO and the amount of $NO_2$ separately, and/or modeling a bulk $NO_x$ output of the engine. Various soot and $NO_x$ estimators are known in the art that can benefit from real-time calibration.

Another modification operation includes the operation 1504 determining an amount of $NO_x$, where the amount of $NO_x$ is determined after a $NO_x$-affecting catalyst and potentially before the $NO_x$-affecting catalyst. The modification operation includes an operation 1508 to modifying a catalyst $NO_x$ storage model, to modify a catalyst $NO_x$ conversion model, and/or to modify a catalyst NO to $NO_2$ conversion model.

The operation 1508 to modify the catalyst $NO_x$ storage model includes determining an actual storage rate based on the observed amounts of $NO_x$ versus the expected $NO_x$, and can include operations such as determining a present storage rate, a total amount of $NO_x$ stored, a total amount of $NO_x$ released, and/or a present release rate of $NO_x$. Models to estimate $NO_x$ storage and release are known in the art and can be calibrated based upon $NO_x$ determinations from a responsive optical sensor that differentiates, for example, $NO_x$ from $NH_3$ (ammonia).

The operation 1508 to modify the catalyst $NO_x$ conversion model includes determining an actual conversion rate based upon the observed amounts of $NO_x$ versus the expected $NO_x$, and potentially further based upon an amount of $NH_3$ and/or an $NH_3$:$NO_x$ ratio at a $NO_x$ conversion catalyst. The operation 1508 to modify the catalyst NO to $NO_2$ conversion model includes determining an actual conversion rate based upon the observed amounts of NO and $NO_2$ versus the expected amounts of NO and $NO_2$. The upstream amounts of NO and $NO_2$ may be measured or estimated (based upon the characteristics of the engine, for example) and the downstream amounts of NO and $NO_2$ are measured.

Figure 13:
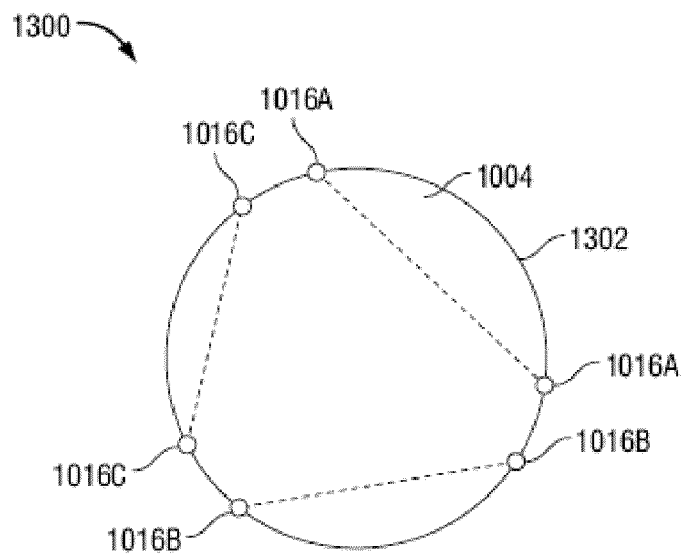
FIG. 13 is a schematic diagram of an apparatus to determine an exhaust gas constituent at spatially divided portions of an exhaust stream.

The technique 1500 includes an operation 1510 to determine the exhaust gas constituent at spatially divided portions of the exhaust stream. Referencing FIG. 13, a cross-section of an exhaust pipe 1302 having an exhaust stream 1004 is shown. A number of optical sensors 1016a, 1016b, 1016c determine an exhaust gas constituent at a number of spatially divided portions of the exhaust stream 1004. The optical sensors 1016a, 1016b, 1016c may be in any configuration to determine the exhaust gas constituent at any position of interest in the exhaust stream 1004. The use of various optical sensors 1016a, 1016b, 1016c distributed spatially around the exhaust stream 1004 allows determination of phenomenon such as mal-distribution of a constituent (e.g. an injected constituent that does not distribute completely around the exhaust stream 1004), puddling of a constituent, and/or accumulation of a constituent.

Figure 14:
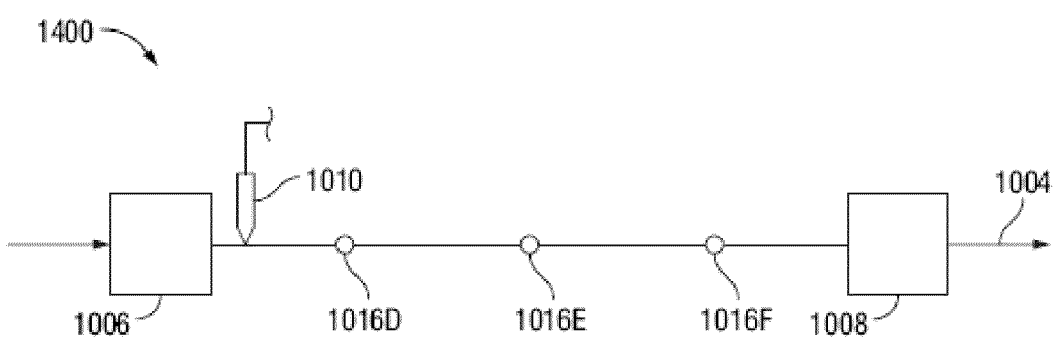
FIG. 14 is a schematic diagram of another apparatus to determine an exhaust gas constituent at spatially divided portions of the exhaust stream.

Referencing FIG. 14, a number of optical sensors 1016d, 1016e, 1016f determine an exhaust gas constituent at a number of spatially divided portions of the exhaust stream 1004. The optical sensors 1016d, 1016e, 1016f may be in any configuration to determine the exhaust gas constituent at any position of interest in the exhaust stream 1004. The use of various optical sensors 1016d, 1016e, 1016f allow determinations of the constituent amount and/or concentration along the axial trajectory of the exhaust stream 104, and allows determination of phenomenon such as deposition or reaction of a constituent in an aftertreatment component, reaction of the constituent in the exhaust stream 1004 (e.g. hydrolysis of urea from an injector 1010), and/or removal of a constituent from the exhaust stream 1004 (e.g. un-evaporated droplets attaching to a sidewall of the exhaust stream 1004 at a bend).

In a non-limiting example, urea is injected at the injector 1010 and the optical sensors 1016d, 1016e, 1016f determine whether the urea hydrolyzes in to ammonia. Where the urea remains along the exhaust stream 1004, hydrolysis determined to be ineffective, where the urea is converted along the exhaust stream 1004, the amount of urea drops and the amount of ammonia increases and the hydrolysis is determined to be effective. Where the urea disappears along the exhaust stream 1004 but ammonia does not appear, it can be determined that the urea is accumulating along the exhaust stream 1004, especially where other information indicates that urea evaporation and hydrolysis may be marginal (e.g. where the temperature of the exhaust stream 1004 is low). The amount of hydrolysis detected is utilized, in one embodiment, the technique 1500 includes an operation 1512 to modify a urea hydrolysis model.

One of skill in the art will understand, based on the disclosures herein, that a combination of radially distributed optical sensors 1016a, 1016b, 1016c and axially distributed optical sensors 1016d, 1016e, 1016f can be utilized to develop a three-dimensional picture of exhaust gas constituent distribution in the exhaust stream 1004.

The detected exhaust gas constituent is urea, and the exhaust gas constituent is detected at a plurality of spatially divided portions of the exhaust stream. The aftertreatment component diagnosis includes diagnosing a urea accumulation condition, urea mal-distribution condition, a urea injector failure condition, and/or a urea hydrolysis failure condition. In certain embodiments, the technique 1500 includes an operation 1514 to diagnose a reductant injector in response to the amount of the exhaust gas constituent. In certain embodiments, the aftertreatment component diagnosis includes diagnosing a composition sensor by determining an amount of the exhaust gas constituent measured by the composition sensor and comparing the reading of the composition sensor to the determined amount of the exhaust gas constituent. For example, the composition sensor can include an oxygen sensor and/or a $NO_x$ sensor.

Any model calibration or modification operations known in the art are contemplated herein including at least modifying a model parameter value, selecting a model from a list of possible models, and/or resetting a model value such as an integrator. Tuning and modification of models are useful provide better real-time performance of the models and related engine and aftertreatment operations, to determine when a component has degraded or failed, to enhance an On Board Diagnostic, to allow the engine or an aftertreatment component to operate in a more efficient manner and/or to allow the engine or an aftertreatment component to compensate for an off-nominal operating condition.

The descriptions which follow, referencing FIGS. 1 through 9, include descriptions of exemplary optical sensors capable of performing in an internal combustion engine exhaust environment, including the temperatures, soot, and other chemical constituents normally found in an engine exhaust environment.

FIG. 1 is a schematic diagram of a system 100 for optically determining fluid constituents in challenging environments, including a fluid conduit receiving exhaust gas from an internal combustion engine. In certain embodiments, the system 100 includes an engine 102 having a sample channel (refer to FIG. 2) comprising a conduit 114 for an engine related fluid. The conduit 114 in the illustration of FIG. 1 is an EGR recirculation path, and the engine fluid in the illustration of FIG. 1 is recirculating exhaust gas flowing in the conduit 114. In certain embodiments, the conduit 114 may be any conduit having an engine related fluid therein, including, without limitation, an exhaust flow path 106, an engine intake path, a fuel line, a coolant line, a portion of an intake manifold, and an intake port for an individual cylinder of a multi-cylinder engine. In certain embodiments, the engine related fluid includes engine exhaust gas, engine oil, engine coolant, recirculating exhaust gas, fuel, engine intake gas, and/or engine intake gas corresponding to a single cylinder of a multi-cylinder engine. In certain embodiments, the system further includes a device 112 for determining a concentration of a constituent of the engine fluid. Reference FIG. 2 for details of an exemplary embodiment of the device 112.

In certain embodiments, the system 100 further includes a controller 118. The controller 118 is structured to determine a concentration of a component of interest in the engine related fluid. The controller 118 includes communications to sensors and actuators throughout the system 100, and such communications may be through networks, datalinks, wireless communications, or other communication methods known in the art. The controller 118 may be a single device or distributed devices. In certain embodiments, the controller 118 includes a computer processor and computer readable memory of any known type. In certain embodiments, the controller 118 includes modules structured to functionally execute procedures performed by the controller. The use of the term modules emphasizes the implementation independence of the procedures. Modules may be elements of computer readable code, and may be grouped, divided, and/or distributed among various devices comprising the controller 118. Reference FIG. 3 for details of an exemplary embodiment of the controller 118.

In certain embodiments, the component of interest includes a nitrogen-oxygen compound, a hydrocarbon, a sulfur containing compound, ammonia, a compound representative of a natural gas content, a carbon-oxygen compound, and/or an amount of particulates. For example, the compound of interest in certain embodiments includes methane and ethane, and the controller 118 calculates a natural gas content in response to the amount of methane and ethane in the engine related fluid. In certain embodiments, the component of interest includes methane, ethane, and/or propane. In certain embodiments, the component includes nitrogen oxide ($N_yO_x$), nitric oxide (NO), nitrogen dioxide ($NO_2$), and/or nitrous oxide ($N_2O$). In certain embodiments, the component of interest includes carbonyl sulfide (O=C=S), carbon monoxide, and/or carbon dioxide.

In certain embodiments, the component of interest is component indicative of engine wear, and the controller 118 is further structured to determine an engine wear index in response to the concentration of the component of interest. For example, the compound of interest may be brass (indicative of wear in certain bearings), iron (indicative of wear in certain engine blocks), a material known to be in the piston rings, and/or any other compound that indicates engine wear in a specific application.

In certain embodiments, the component of interest includes a component indicative of fuel quality, and the controller 118 is further structured to determine a fuel quality index in response to the concentration of the component of interest. For example, the compound of interest may be nitrogen which in certain applications is indicative of a filler used in natural gas fuels. The concentration of nitrogen in the natural gas, in certain embodiments, can be indicative of the fuel quality. In another example, the compound of interest may correspond to an additive, tracer, aromatic compound, or other compound in the fuel that in specific applications may be indicative of a quality of the fuel.

In certain embodiments, the engine related fluid includes engine fuel or engine oil, and the component of interest includes sulfur or a sulfur compound. In certain embodiments, the amount of sulfur allowed in the engine fuel and/or engine oil may be regulated, and the controller 118 determines the concentration of sulfur in the fuel and/or oil to provide that information to an engine controller (not shown, but may be included in the controller 118) for appropriate response.

In certain embodiments, the engine related fluid includes engine oil, and the component of interest comprises one of water and ethylene glycol. In certain embodiments, the presence of coolant in engine oil may be indicative of certain types of failure, and the controller 118 determines the concentration of sulfur in the fuel and/or oil to provide that information to an engine controller (not shown, but may be included in the controller 118) for appropriate response.

In certain embodiments, the engine related fluid includes engine coolant, the component of interest includes a component indicative of engine coolant quality, and the controller 118 is further structured to determine an engine coolant quality index in response to the concentration of the component of interest. The engine coolant quality, for example, may be a description of the water/ethylene glycol ratio, and may be utilized by the engine controller (not shown, but may be included in the controller 118), for example in a warranty assessment after an engine failure.

In certain embodiments, the engine related fluid includes engine oil, the component of interest includes a component indicative of engine oil quality, and the controller is further structured to determine an engine oil quality index in response to the concentration of the component of interest. For example, the component of interest may track the present concentration of an additive in the oil to determine when the oil should be changed. In another example, the component of interest may include a compound or group of compounds from which an API number or other characteristic of the oil may be determined to evaluate the quality of the oil. In certain embodiments, the engine related fluid includes a engine oil, engine fuel, engine coolant, an exhaust gas fluid, a recirculating exhaust gas fluid, and/or an engine intake fluid.

Figure 2:
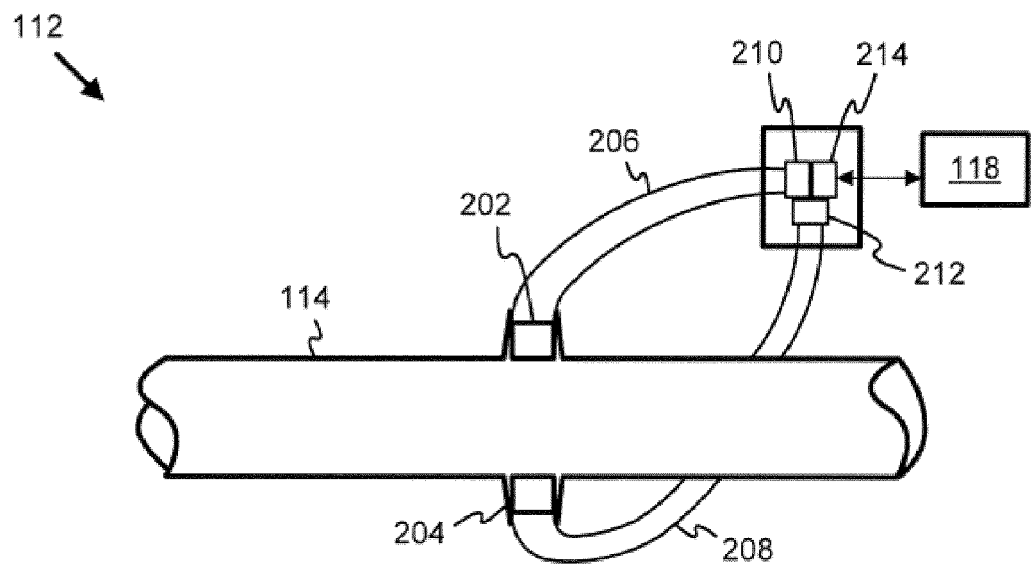
FIG. 2 is a schematic illustration of an device for detecting engine fluid constituents.

FIG. 2 is a schematic illustration of a device 112 for detecting engine fluid constituents. The device 112 includes an electromagnetic (EM) source 214 structured to emit EM radiation through a first metal tube 206. The EM radiation includes EM energy at a wavelength of interest. In certain embodiments, the EM energy may be provided by a broad spectrum EM source (e.g. an incandescent source) and passed through an interference filter 210 to remove frequencies outside the wavelength of interest. In certain embodiments, the interference filter 210 is a bandpass filter removing frequencies outside a desired range of frequencies. In certain embodiments, the EM source 214 is a laser that emits the EM radiation at a wavelength of interest and may not include an interference filter 210. In certain embodiments, the EM source 214 is a tunable laser that emits EM radiation at a number of frequencies of interest, for example to detect a number of components of interest. In certain embodiments, the EM source 214 includes a plurality of source that each emit a different wavelength, or the EM source 214 may be a broad spectrum emitter (e.g. the incandescent source), and a plurality of interference filters 210 allow different wavelength ranges to the first metal tube 206 at different times to detect different components of interest.

In certain embodiments the EM source 214 includes at least one of a laser device, a light emitting diode, and a gallium arsenide light emitting diode. In certain embodiments, the device 112 includes the interference filter 210 disposed between the EM source 214 and the sample channel 114, with the interference filter 210 including a band pass filter. In certain embodiments, the first metal tube 206 and the second metal tube 208 each comprise extruded aluminum, extruded stainless steel, a polished metal, and/or a machined metal. The tubes 206, 208 should have sufficient resistance to temperature and corrosion in the system 100, and have sufficient internal reflectivity to convey the EM radiation to the sample channel 114 and back from the sample channel 114.

In certain embodiments, the device 112 further includes an EM detector 212 structured to receive a remainder radiation through a second metal tube 208, the remainder radiation including the remaining EM energy of the EM radiation after passing through the sample channel 114. In certain embodiments, the second metal tube 208 may be the same physical tube as the first metal tube 206, for example the EM radiation may pass through the first metal tube 206, reflect off a mirror opposing the entrance of the first metal tube 206, and pass back into the first metal tube 206, which is then acting as the second metal tube 208, back to the EM detector 212. In certain embodiments, the EM detector 212 includes a lead selenide detection device.

In certain embodiments, the device 112 includes a first window 202 isolating the first metal tube 206 from the sample channel 114, and a second window 204 isolating the second metal tube 208 from the sample channel 114. The window material should be selected to allow sufficient EM energy through the window 202, 204 at the wavelength of interest that the EM detector 212 can distinguish the concentration of the component of interest through the expected operational range for the component of interest, or the portion of the expected operational range that is of interest. For example, if the component of interest is oxygen in an internal combustion engine application, the expected range may be zero to twenty-one percent oxygen by mole, or a lower range if, for example, values above a certain percentage are not of interest in a particular application.

Factors that affect the final strength of the received EM radiation include the available power of the EM source 214, losses in the interference filter 210, tubing 206, 208, the strength of the extinction response of the component of interest at the selected wavelength, and the optical path length across the sample channel 114. The material of the window 202, 204 should further be a material that withstands the thermal and chemical environment of the conduit 114, and further that can suitably conduct heat to allow a cleaning event (e.g. reference FIGS. 3 and 9, and related descriptions) and withstand the cleaning temperature of the cleaning event. The selection of a specific window material is dependent upon the application and is a mechanical step for one of skill in the art based upon the disclosures herein. In certain embodiments, the first window 202 and the second window 204 comprise a material selected from the group consisting of sapphire, glass, and diamond. In one example, the component of interest is carbon dioxide, the engine related fluid includes combustion exhaust gases, the wavelength of interest is about 4.26µ, the sample channel 114 has an optical path length of about 35 mm, and the window 202, 204 material is sapphire.

In certain embodiments, the first window 202 and the second window 204 are the same physical window, for example where the first metal tube 206 and the second metal tube 208 are the same physical tube. In certain embodiments, the device 112 includes a reflective device (e.g. a mirror, not shown) opposing the first window 202, for example where the first metal tube 206 and the second metal tube 208 are the same physical tube.

In certain embodiments, the system further includes a kit (e.g. as a portion of the device 112) having the first metal tube 206, the second metal tube 208, the first window 202, the second window 204, and at least a portion of the sample channel 114. In certain embodiments, the kit further includes means for quick removal and replacement. For example, the kit may include wing nuts, levered clamps, seals, and/or other quick disconnect devices to allow ready removal of the kit and installation of a replacement kit. In certain embodiments, means for quick removal and replacement further includes positioning of the device 112 within a system at a location where access is readily available—for example positioning the device where the starter, turbocharger 110, fan, or other components in the application are not blocking access to the kit.

Figure 3:
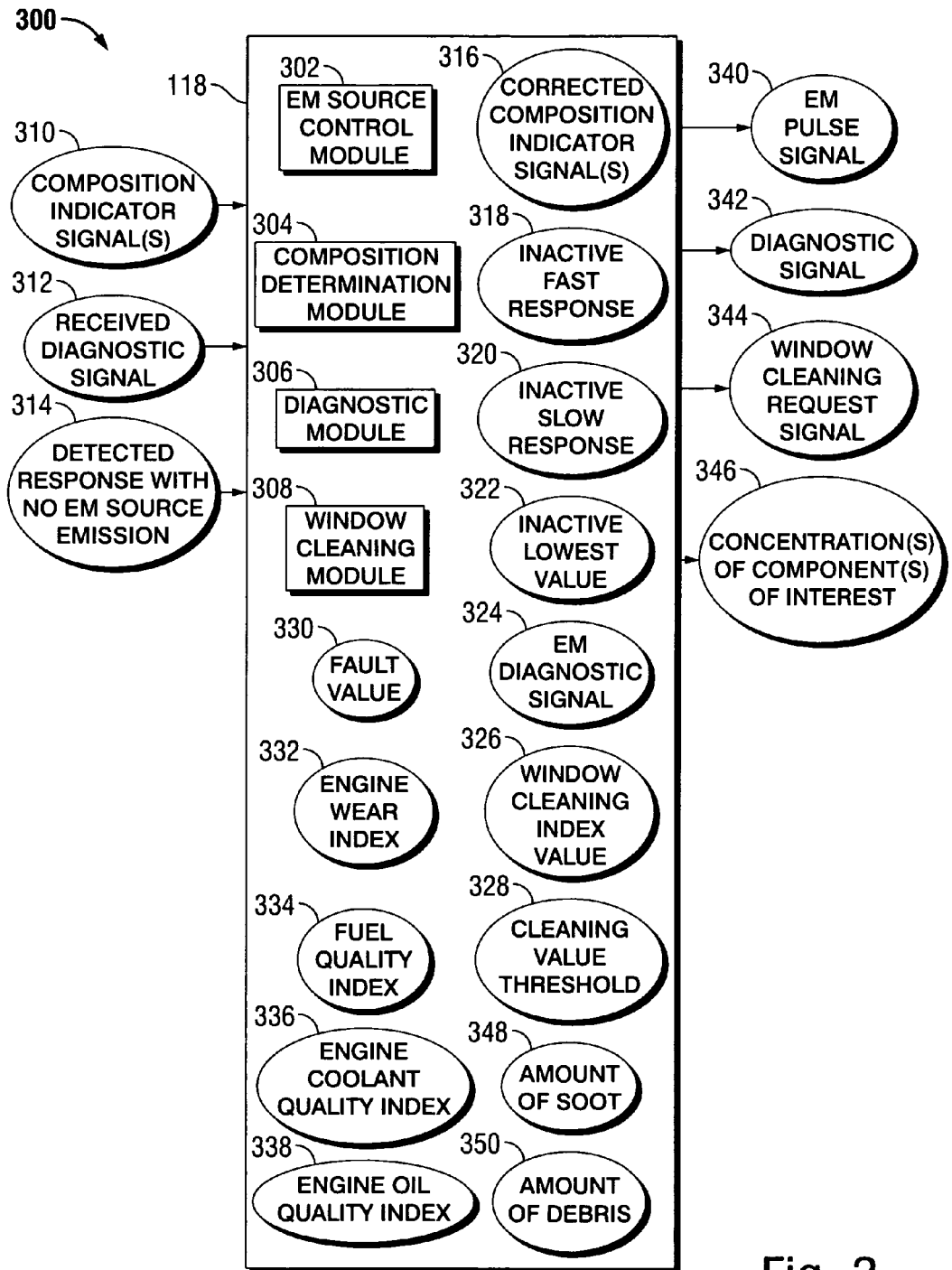
FIG. 3 is a schematic diagram of a controller structured to determine a concentration of a component of interest.

FIG. 3 is a schematic diagram of a controller 118 structured to determine a concentration of a component of interest. In certain embodiments, the controller 118 is structured to determine a composition indicator signal 310 in response to a strength of the remainder radiation and determine a concentration of a component of interest 346 according to the composition indicator signal 310. For example, an EM detector 212 receives the EM remainder radiation, the controller 118 determines the composition indicator signal 310 based on the strength of the remainder radiation, and determines the concentration of a component of interest 346 according to the composition indicator signal 310.

In certain embodiments, a controller 118 includes an electromagnetic (EM) source control module 302 structured to provide an EM pulse signal 340. In certain embodiments, the EM source 214 emits EM radiation through the first metal tube 206 and the sample channel 114 in response to the EM pulse signal 340. In certain embodiments, the EM detector 212 receives the EM radiation from the sample channel 114 through a second metal tube 208, and provides a composition indicator signal 310 in response to a remaining radiation strength at the wavelength of interest. In certain embodiments, the controller 118 includes a composition determination module 304 that determines a concentration of a component of interest 346 according to the composition indicator signal 310. For example, in certain embodiments, the composition indicator signal 310 may be an extinction value at the wavelength of interest, and the composition determination module 304 may utilize a lookup table that determines the concentration of a component of interest 346 as a function of the extinction value. The lookup table is calibrated according to the system 100 that the device 112 is installed in.

In certain embodiments, the EM source control module 302 provides an EM diagnostic signal 342, and the EM source 214 emits an EM diagnostic radiation in response to the EM diagnostic signal. The EM diagnostic radiation includes energy at a diagnostic wavelength, and the EM detector 212 provides a received diagnostic signal 312 in response to a remaining EM diagnostic radiation strength at the diagnostic wavelength. The diagnostic wavelength is a wavelength selected such that no expected components of the engine related fluid significantly absorb the diagnostic wavelength, except for "grey" or "black" components (e.g. components that absorb all wavelengths roughly equivalently). In many circumstances, soot in the engine related fluid and debris deposited on the windows 202, 204 can be treated as grey matter with sufficient accuracy for many purposes.

In certain embodiments, the controller 118 further includes a diagnostic module 306 that determines an amount of soot 348 in response to the received diagnostic signal 312. In certain embodiments, the amount of soot 348 is determined by attributing an entire diagnostic signal 312 strength loss, relative to a baseline diagnostic signal 312 strength, to absorption by soot in the engine related fluid. In certain embodiments, the diagnostic module 306 determines an amount of debris 350 deposited on the windows (202, 204), determines a diagnostic signal 312 strength loss attributable to the amount of debris 350, and determines a remainder of the diagnostic signal 312 strength loss as attributable to the amount of soot 348.

In certain embodiments, the composition determination module 304 determines the concentration of the component of interest 346 according a corrected composition indicator signal 316. In certain embodiments, the composition determination module 304 determines the corrected composition indicator signal 316 according to the equation:

$$CCIS = \frac{Active - Dark}{Inactive - Dark} \quad \text{(Equation 1)}$$

In the example Equation 1, CCIS is the corrected composition indicator signal 316, Active is the composition indicator signal 310, Inactive is the received diagnostic signal 312, and Dark is a detected response at a time when the EM source 214 is not emitting EM radiation. For example, if the composition indicator signal 310 shows 70% (i.e. 30% absorption of the wavelength of interest), the received diagnostic signal 312 shows 90%, and the baseline response with the EM source 214 turned off is 2%, the composition indicator signal 310 is a value based on 70% while the corrected composition indicator signal 316 is a value based on ((70−2)/(90−2)) is 77%, or a little stronger than the directly indicated composition indicator signal 310 due to suppression of the signal by an amount of soot 348 and/or an amount of debris 350.

In certain embodiments, the diagnostic module 306 determines the amount of soot 348 by filtering the received diagnostic signal 312 with a time constant less than 30 seconds to provide an Inactive fast response signal 318, filtering the received diagnostic signal 312 with a time constant greater than 30 seconds to provide an Inactive slow response signal 320, and determining the amount of soot 348 according to the Inactive slow response signal 320 subtracted from the Inactive fast response signal 318. The 30-second value is exemplary only. The Inactive fast response signal 318 is an indicator of total grey matter in the conduit 114 (i.e. soot plus debris) and the inactive slow response signal 320 is an indicator of long term grey matter in the conduit 114 (i.e. debris only). In certain embodiments, the inactive slow response 320 utilizes a relatively slow rising time constant and a relatively fast falling time constant, to bias the inactive slow response 320 to a lower value in the observed range of inactive values (i.e. of received diagnostic signal 312 values). In certain embodiments, diagnostic module determines an amount of debris 350 accumulated on the window(s) 202, 204 according to a lowest Inactive value 322 observed over time. For example, the diagnostic module 306 may track received diagnostic values 312, and reset the inactive lowest value 322 to the lowest observed value over a recent period—for example a lowest value observed in the last five minutes, or a lowest value observed during the most recent engine motoring event (i.e. when the engine was last not combusting any fuel).

In certain embodiments, the controller 118 further includes a window cleaning module 308 that provides a window cleaning index value 326 in response to the amount of debris 350 accumulated. In certain embodiments, the window cleaning module 308 is further structured to provide a window cleaning request signal 344 in response to the window cleaning index value 326 exceeding a cleaning threshold value 328. In certain embodiments, the system 100 includes a window cleaning means that cleans the window(s) in response to the window cleaning request signal 344.

In certain embodiments, the diagnostic module 306 determines a fault value 330, an engine wear index 332, a fuel quality index 334, an engine coolant quality index 336, and/or an engine oil quality index 338 in response to the concentration of the component of interest 346. In certain embodiments, the fault value 330 is an indication whether an engine 102 parameter is out of tolerance according to the concentration(s) of the component(s) of interest 346. In certain embodiments, the indices 332, 334, 336, 338 provide a value correlated to the underlying engine parameter—i.e. engine wear, fuel quality, engine coolant quality, and/or engine oil quality—according to the concentration(s) of the component(s) of interest 346.

Figure 4:
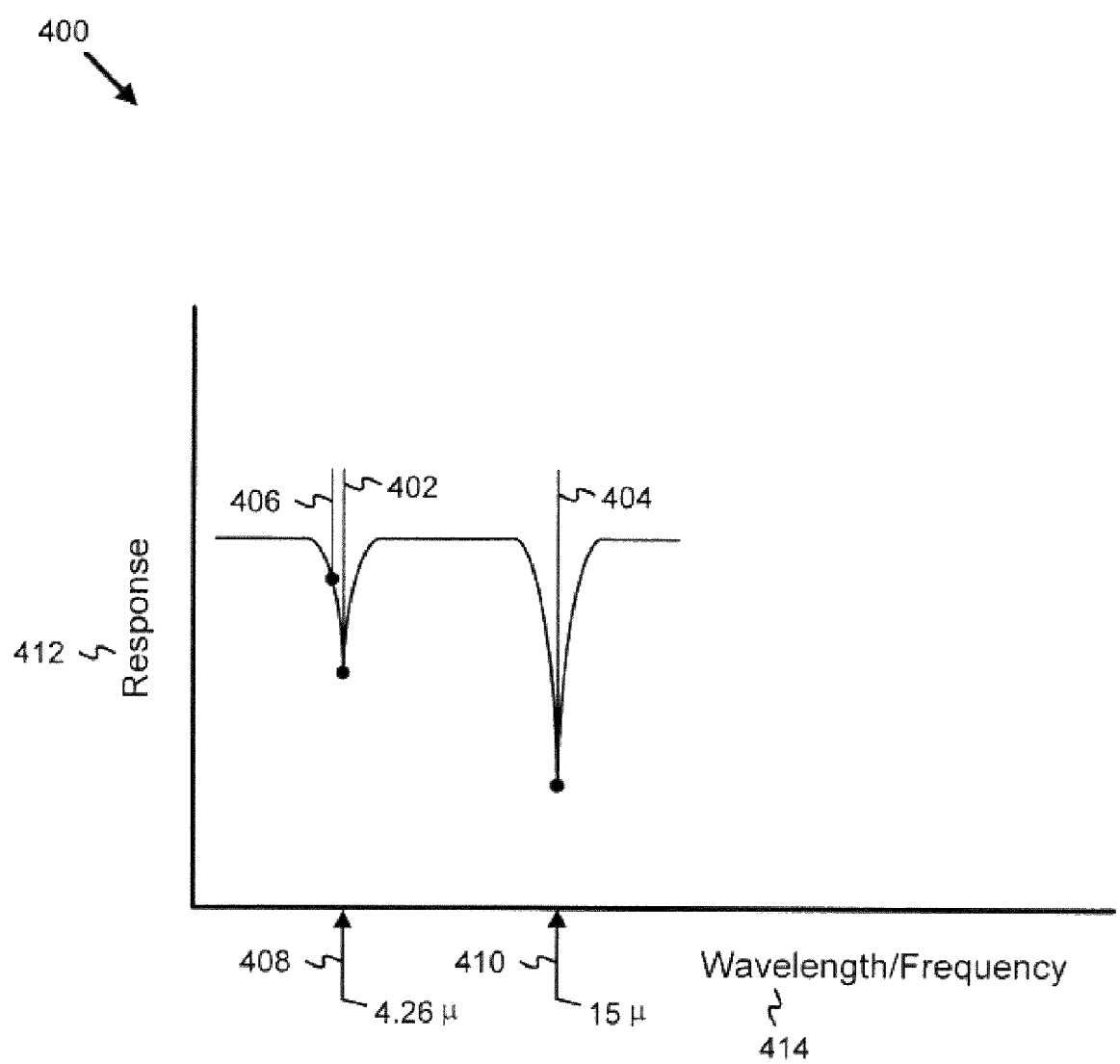
FIG. 4 is an illustration of a constituent wavelength response.

FIG. 4 is an illustration 400 of a constituent wavelength response. The illustration 400 includes a response value 412 versus a wavelength (or possibly frequency) value 414 for a component of interest. The constituent wavelength response illustrated in FIG. 4 is consistent with a simplified illustration for carbon dioxide, showing a first responsive wavelength 408 and a second, stronger, responsive wavelength 410. Depending upon the parameters of the system 100 (refer to the section referencing FIG. 2), a wavelength of interest for the EM radiation from the EM source 214 may be selected at either responsive wavelength 402, 404. In certain embodiments, the sample channel 114 may be too long, or the constituent concentrations expected may be too high, such that instead of using the stronger response wavelength 410, the weaker response wavelength 408 may be selected.

In certain embodiments, the wavelength of interest may be selected as one of the responsive wavelengths, for example selecting wavelength 402 and/or 404. In certain embodiments, the wavelength of interest may be selected as a wavelength near one of the responsive wavelengths, for example selecting wavelength 406. In certain embodiments, the wavelength of interest such that an extinction of the wavelength of interest is about 50% of an extinction of the responsive wavelength near the wavelength of interest (e.g. about what the wavelength of interest 406 indicates in FIG. 4). The extinction of the responsive wavelength may be measured as a peak value (e.g. a discrete value right on the responsive wavelength 408), or as an area under (or above) a range of wavelength values, such as a range of values allowed through the band-pass filter 210.

The selection of an off-nominal wavelength such as the wavelength of interest 406 allows for longer sample channel 114 lengths, detection at higher constituent concentrations, and similar adjustments. The wavelength of interest may be variable or multiple in certain embodiments, for example providing higher extinction rates at lower constituent concentrations and lower extinction rates at higher constituent concentrations, or providing higher and lower extinction rates at all times and utilizing both extinction rates in calculating a composition indicator signal 310. In certain embodiments, the responsive wavelength includes a fundamental wavelength and/or a harmonic wavelength.

The schematic flow diagrams (FIGS. 5-9) and related descriptions which follow provide illustrative embodiments of operations related to the present application. Operations shown are understood to be illustrative only, and operations may be combined or divided, and added or removed, as well as re-ordered in whole or part, unless stated explicitly to the contrary herein.

Figure 5:
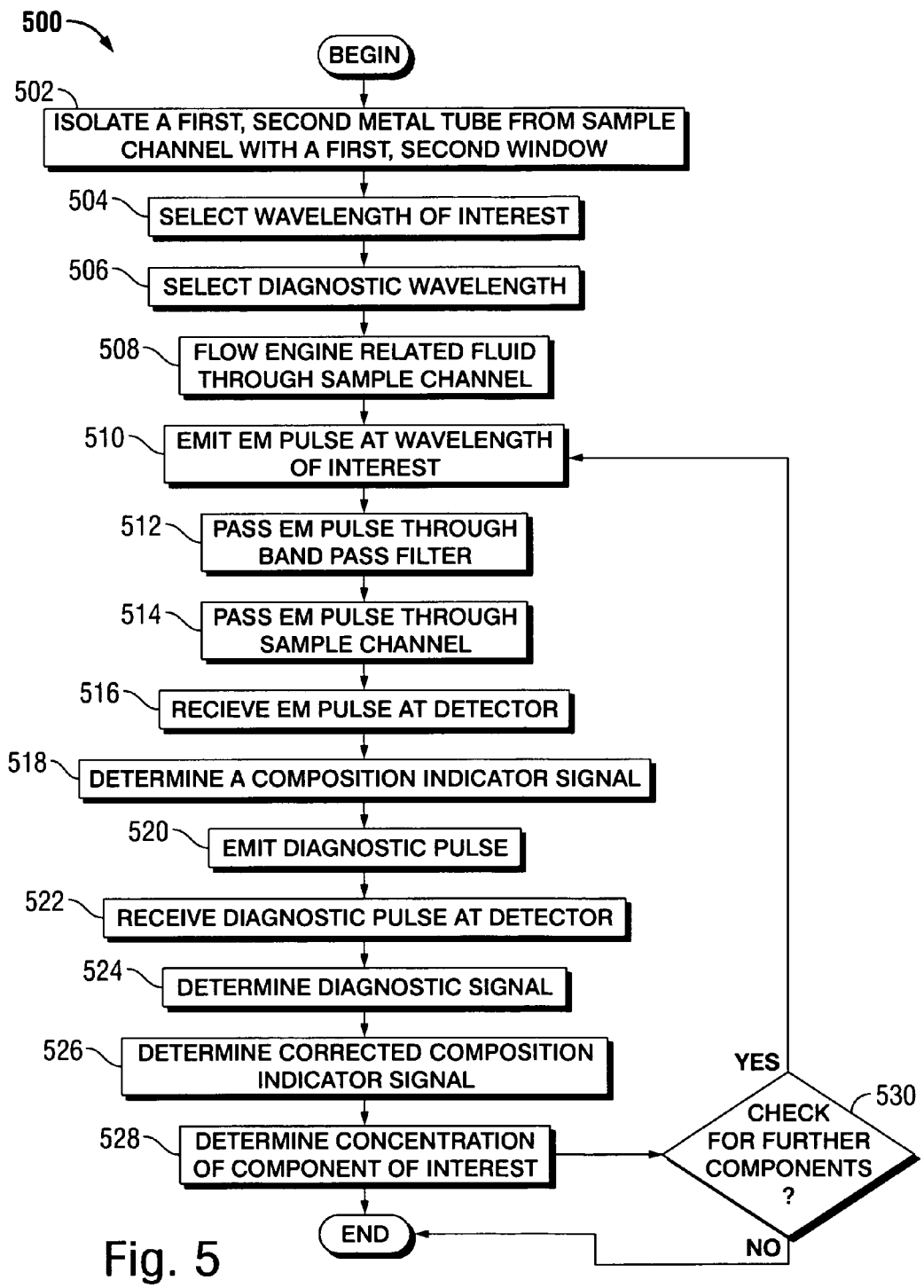
FIG. 5 is a schematic flow diagram of a procedure for determining a concentration of a component of interest.

FIG. 5 is a schematic flow diagram of a procedure 500 for determining a concentration of a component of interest. In certain embodiments, the procedure 500 includes an operation 502 to isolate the first metal tube from the sample channel with a first window and isolating the second metal tube from the sample channel with a second window. In certain embodiments, the procedure 500 further includes an operation 504 to select a wavelength of interest, and an operation 506 to select a diagnostic wavelength.

The procedure 500 includes an operation 508 to flow an engine related fluid through a sample channel, and an operation 510 to emit an electromagnetic (EM) radiation comprising energy at a wavelength of interest through a first metal tube. The procedure 500 further includes an operation 512 to pass the EM radiation through a bandpass filter. The procedure 500 further includes an operation 514 to pass the EM radiation through the sample channel and an operation 516 to receive the radiation at an EM detector through a second metal tube. The procedure 500 further includes an operation 518 to determine a composition indicator signal in response to a remaining radiation strength at the wavelength of interest.

In certain embodiments, the procedure 500 includes an operation 520 to emit an EM diagnostic radiation comprising energy at a diagnostic wavelength, and an operation 522 to receive the remaining diagnostic radiation strength at the diagnostic wavelength at an AM detector. In certain embodiments, the procedure 500 further includes an operation 524 to determine a diagnostic signal in response to the remaining diagnostic radiation strength at the diagnostic wavelength. In certain embodiments, the procedure 500 further includes an operation 526 to determine a corrected composition indicator signal. The procedure further includes an operation 528 to determine a concentration of a component of interest according to the composition indicator signal by utilizing the corrected composition indicator signal. In certain embodiments, the procedure 500 further includes an operation 530 to check for whether concentrations should be determined for further components. In response to a determination that concentrations should be determined for further components, the procedure 500 includes operations 510-528 to emit EM radiation at a second (or third, fourth . . . etc.) wavelength of interest, and to determine a concentration of a second component of interest in response to the EM radiation at the second wavelength of interest.

Figure 6:
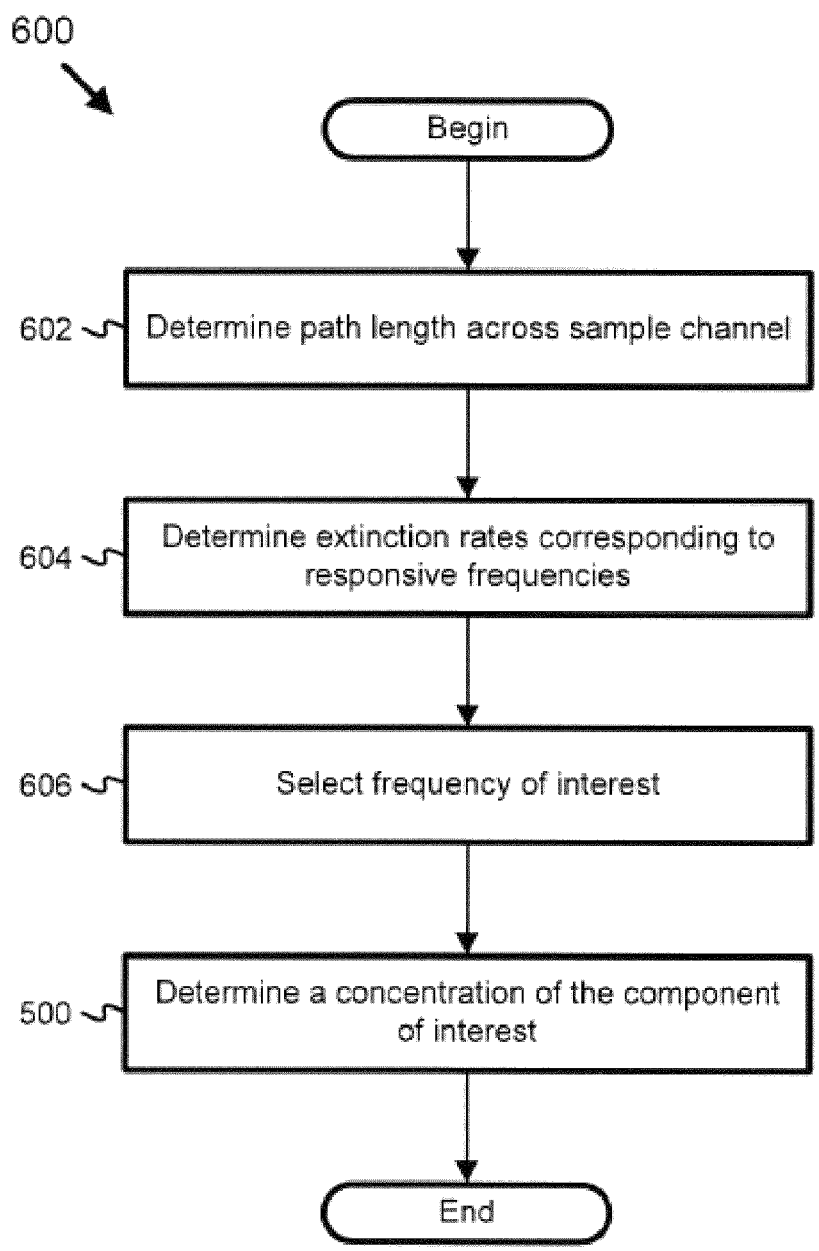
FIG. 6 is a schematic flow diagram of a procedure for designing an apparatus for determining a concentration of a component of interest.

FIG. 6 is a schematic flow diagram of a procedure 600 for designing an apparatus for determining a concentration of a component of interest. The procedure 600 includes an operation 602 to determine a path length across a sample channel, and an operation 604 to determine extinction rates corresponding to responsive wavelengths for a component of interest at a design range of concentration. The procedure 600 further includes an operation 606 to select a frequency of interest according to the extinction rates corresponding to the responsive frequencies for the component of interest at the design range of concentrations of the component of interest. In certain embodiments, the procedure 600 includes an operation 500 to determine a concentration of a component of interest, for example utilizing one or more operations from the procedure 500.

Figure 7:
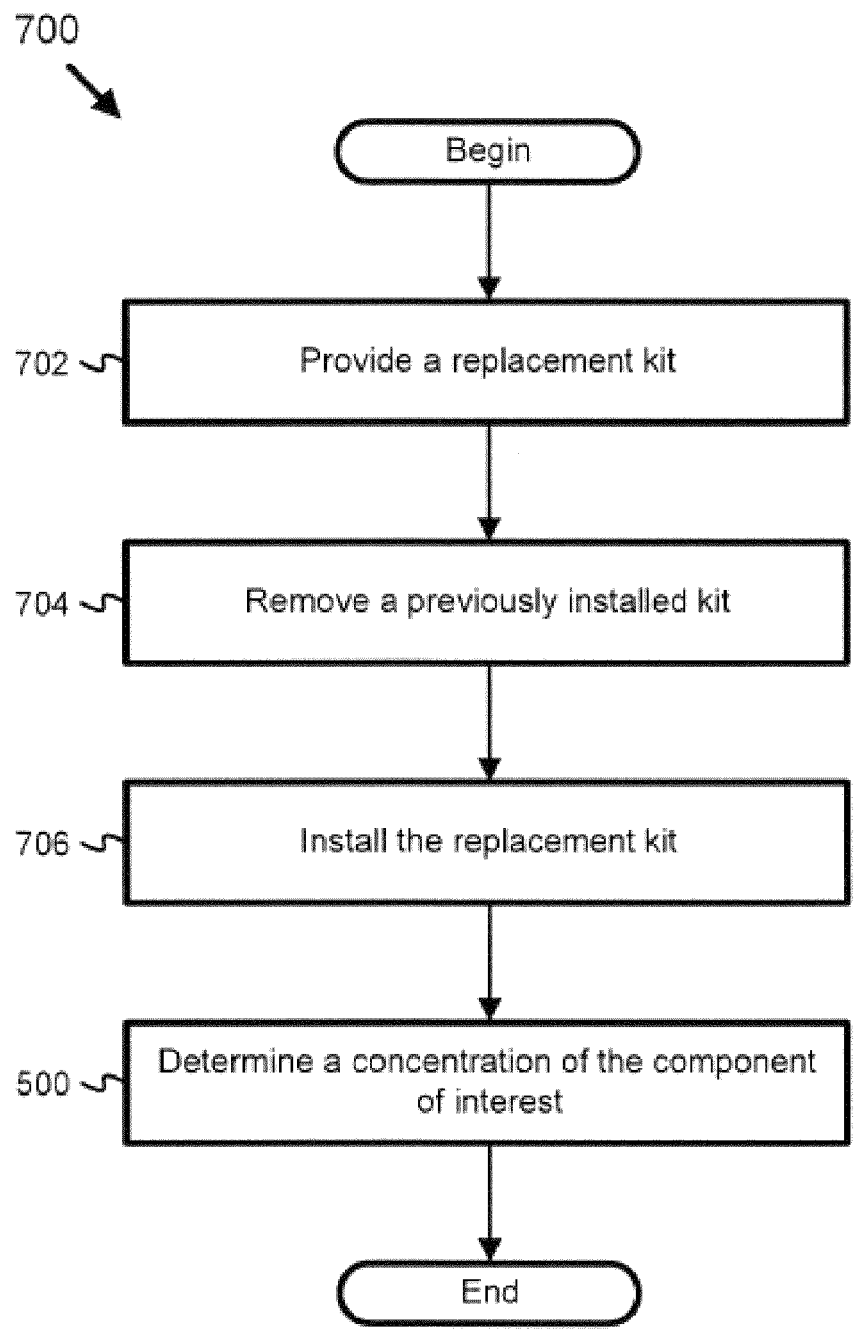
FIG. 7 is a schematic flow diagram of a procedure for replacing an apparatus for determining a concentration of a component of interest.

FIG. 7 is a schematic flow diagram of a procedure 700 for replacing an apparatus for determining a concentration of a component of interest. In certain embodiments, the procedure 700 includes an operation 702 to provide a replacement kit comprising the first metal tube, the second metal tube, the first window, and the second window, and operations 704 including removing a previously installed kit from an engine. The procedure 700 further includes an operation 706 to install the replacement kit on the engine. In certain embodiments, the procedure 700 includes an operation 500 to determine a concentration of a component of interest, for example utilizing one or more operations from the procedure 500.

Figure 8:
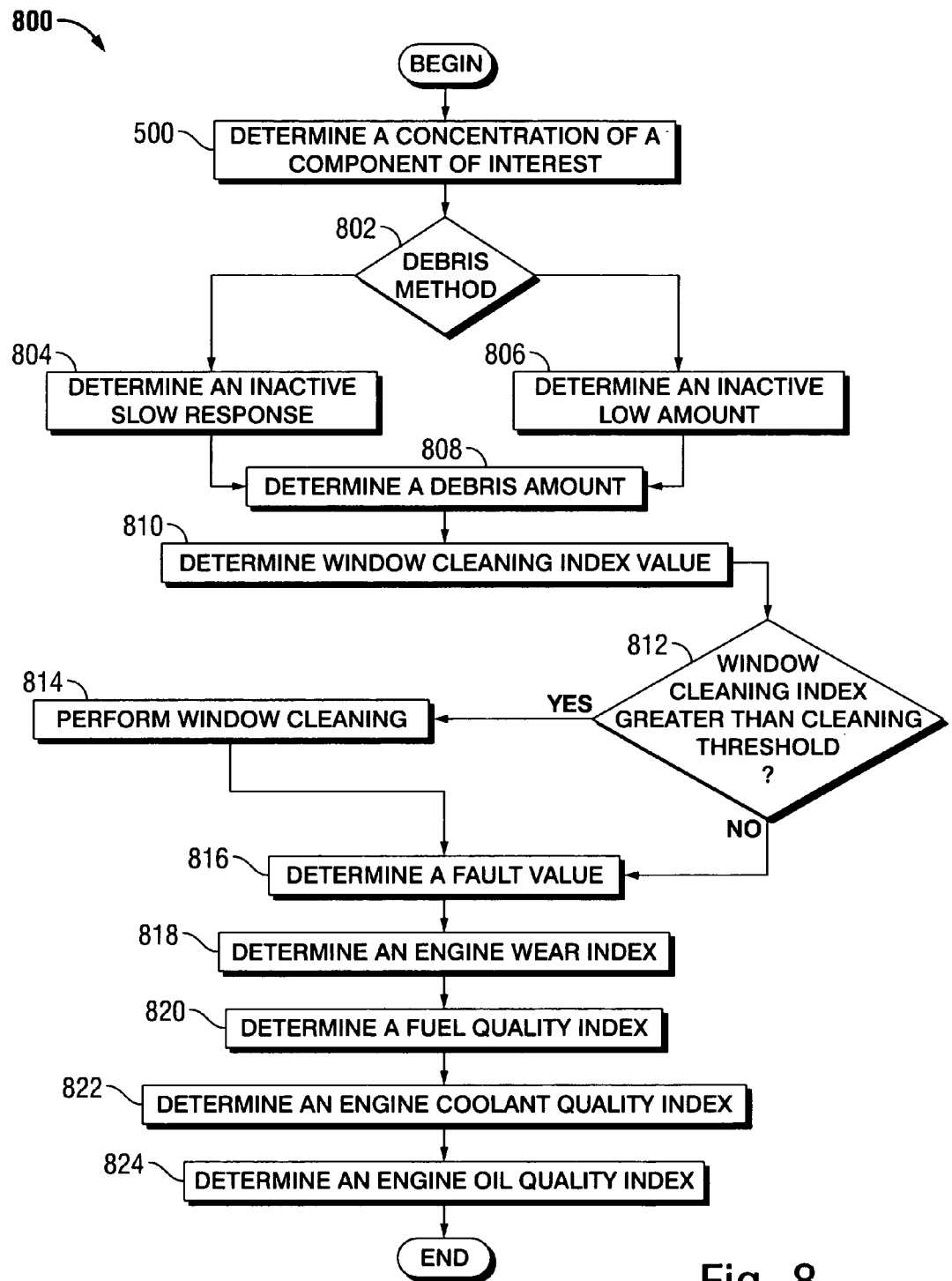
FIG. 8 is a schematic flow diagram of a procedure for determining a plurality of fluid indices.

FIG. 8 is a schematic flow diagram of a procedure 800 for determining a plurality of fluid indices. In certain embodiments, the procedure 800 includes an operation 500 to determine a concentration of a component of interest, for example utilizing one or more operations from the procedure 500. In certain embodiments, the procedure 800 further includes an operation 802 to determine whether a debris determination method includes an inactive slow response or an inactive low amount. In response to the procedure 800 including the inactive slow response, the procedure 800 includes an operation 804 to determine an inactive slow response, and an operation 808 to determine a debris amount in response to the inactive slow response. In response to the procedure 800 including an inactive low amount, the procedure 800 includes an operation 806 to determine an inactive low amount, and an operation 808 to determine a debris amount in response to the inactive low amount.

In certain embodiments, the procedure 800 includes an operation 810 to determine a window cleaning index value in response to the amount of debris accumulated. In certain embodiments, the procedure 800 further includes an operation 812 to determine whether the window cleaning index is greater than a cleaning threshold. In certain embodiments, the procedure 800 includes an operation 814 to perform a window cleaning event in response to determining the window cleaning index value exceeds a cleaning threshold value. In certain embodiments, the procedure includes an operation 816 to determine a fault value in response to the received diagnostic signal. In certain embodiments, the procedure 800 includes an operation 818 to determine an engine wear index 818, an operation 820 to determine a fuel quality index, an operation 822 to determine an engine coolant quality index, and/or an operation 824 to determine an engine oil quality index in response to the concentration(s) of the component(s) of interest.

Figure 9A:
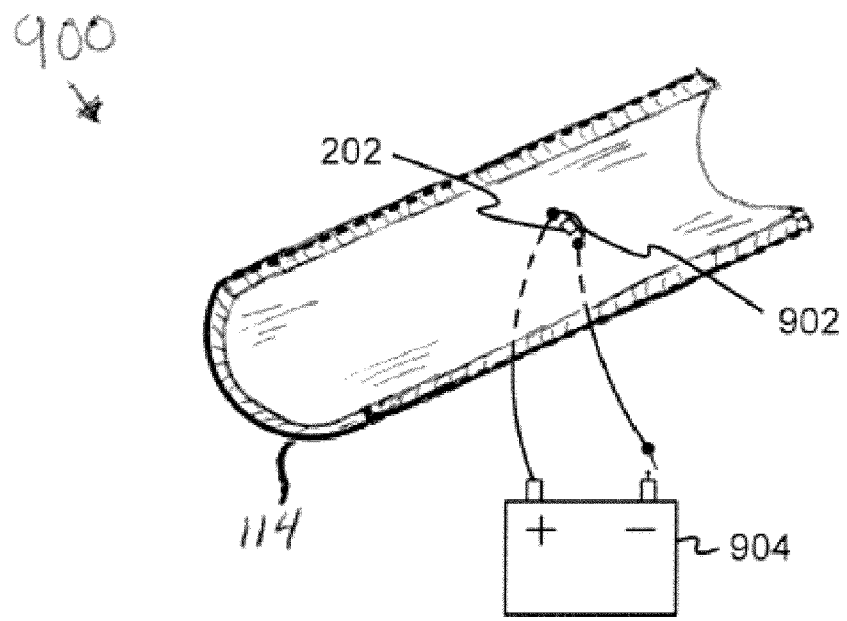
FIG. 9A is a schematic diagram of an apparatus for cleaning an optical element.

FIG. 9A is a schematic diagram of an apparatus for cleaning an optical element. The apparatus 900 includes the optical element 202 and a means for cleaning the optical element. In certain embodiments, the apparatus 900 includes a wire 902 with a high thermal expansion coefficient, and the wire is positioned to sweep the optical element 202 upon a temperature increase event. In certain embodiments, the wire 902 may be a resistive wire that heats when a supply voltage 904 is applied, sweeping the wire 902 across the optical element 202.

Figure 9B:
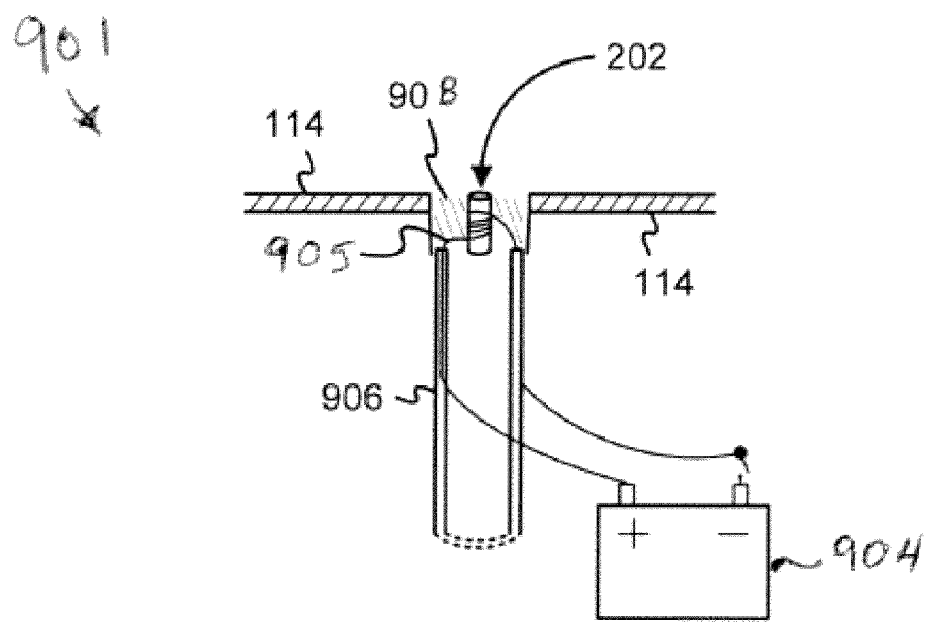
FIG. 9B is a schematic diagram of an apparatus for cleaning an optical element.

FIG. 9B is a schematic diagram of an apparatus for cleaning on optical element. The apparatus 901 includes the optical element 202, which may be a sapphire cylinder. In certain embodiments, and a tube 206. In certain embodiments, a ceramic filler 908 or other heat resistant material provides a seal between the optical element 202 and the conduit 114. The apparatus 901 includes a means for cleaning the optical element 202 including a resistive wire 905 wrapped around a portion of the optical element 202, such that when the resistive wire 905 is heated the face of the optical element 202 exposed to the conduit 114 (i.e. the "window") is heated sufficiently to drive debris (through oxidation, evaporation, or other means) from the face of the optical element 202. A supply voltage 904 may be applied to the resistive wire 905 at times where a cleaning event is performed.

Figure 9C:
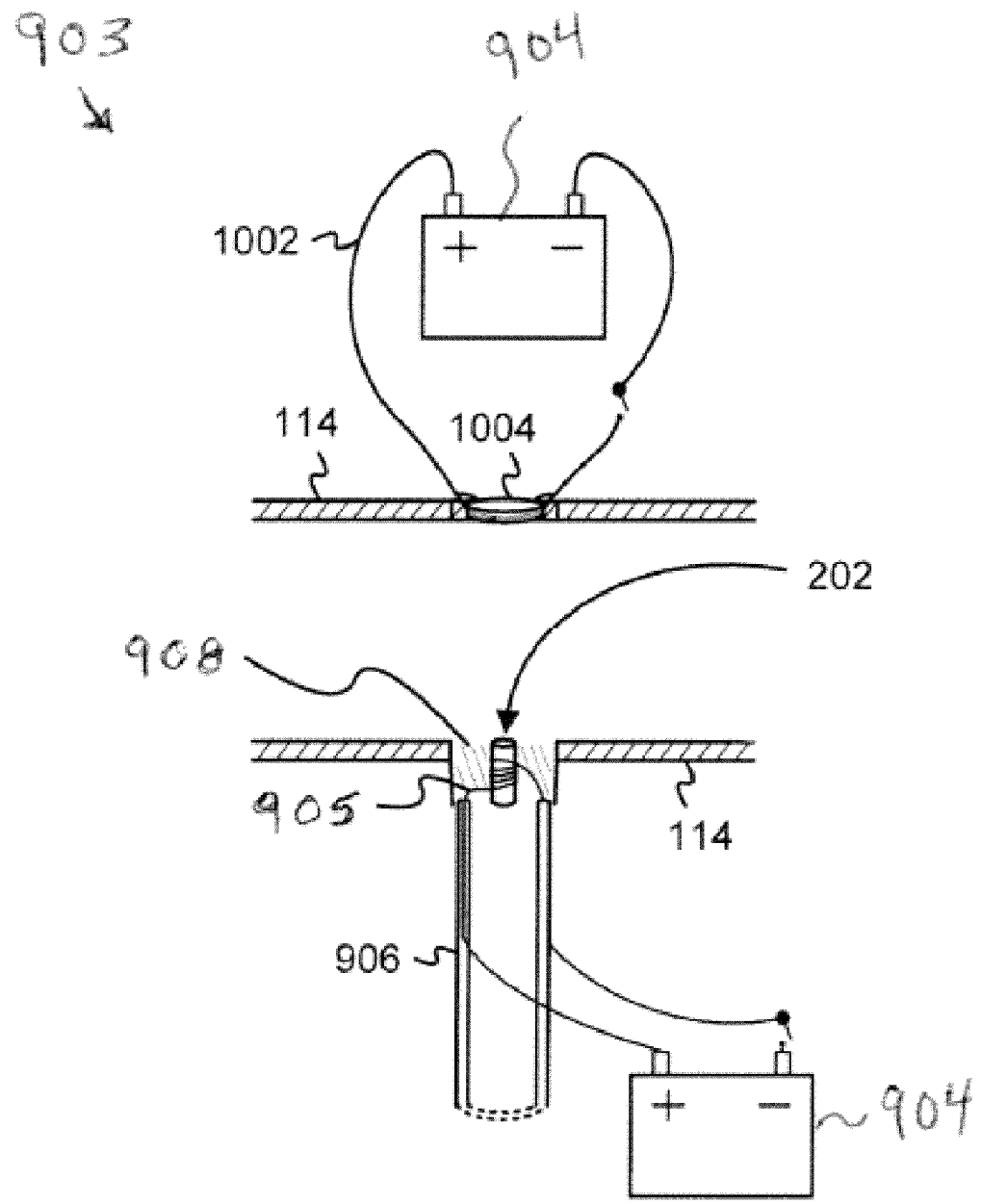
FIG. 9C is a schematic diagram of an apparatus for cleaning an optical element.

FIG. 9C is a schematic diagram of an apparatus 903 for cleaning an optical element. The apparatus 903 includes a resistive wire 910 in thermal contact with a mirror 912 positioned opposite an optical element 202. The resistive wire 910 heats the mirror 912 sufficiently to drive debris (through oxidation, evaporation, or other means) from the face of the mirror 912. A supply voltage 904 may be applied to the resistive wire 910 at times where a cleaning event is performed.

As is evident from the Figures and text presented above, a variety of embodiments according to the present invention are contemplated. Certain exemplary embodiments of methods and apparatus for diagnosing an aftertreatment component, for adjusting an engine operating parameter in response to a component performance description of an aftertreatment component, and for modifying a model stored on a computer readable medium are described. All embodiments are exemplary and non-limiting.

An exemplary method includes providing an exhaust stream for an internal combustion engine, the exhaust stream fluidly coupled to an aftertreatment component, optically determining an amount of an exhaust gas constituent in the exhaust stream, and diagnosing an aftertreatment component in response to the amount of the exhaust gas constituent. In one embodiment, the exhaust gas constituent includes $NO_x$, and diagnosing the aftertreatment component includes determining a catalyst effectiveness. The catalyst effectiveness may be a catalyst adsorption effectiveness and/or a catalyst conversion effectiveness.

In certain embodiments, the exhaust gas constituent is soot. The exemplary method further includes diagnosing the aftertreatment component by determining that a soot filter has failed, and/or by determining a size of the soot. The method further includes determining a source of the soot in response to the size of the soot.

In an exemplary embodiment, the exhaust gas constituent includes NO (nitrogen-oxide), the method includes determining an amount of $NO_2$, and diagnosing the aftertreatment component includes determining a catalyst NO to $NO_2$ conversion effectiveness. In another exemplary embodiment, the exhaust gas constituent includes urea, and diagnosing the aftertreatment component includes determining a urea injector compliance and/or diagnosing an injected urea composition.

In certain embodiments, the exhaust gas constituent is urea, and the method further includes determining the exhaust gas constituent at a plurality of spatially divided portions of the exhaust stream. Diagnosing the aftertreatment component further includes diagnosing a urea accumulation condition, urea mal-distribution condition, a urea injector failure condition, and/or a urea hydrolysis failure condition. In certain embodiments, the method includes diagnosing the aftertreatment component by diagnosing a composition sensor.

Another exemplary embodiment is an apparatus including an optical sensor structured to determine an amount of an exhaust gas constituent in an exhaust stream of an internal combustion engine, a performance analysis module that determines a component performance description in response to the amount of the exhaust gas constituent, and a performance feedback module that adjusts an engine operating parameter in response to the component performance description. The apparatus includes the component performance description as a functional performance description of a physical component. The physical component includes a $NO_x$ adsorption catalyst, a $NO_x$ conversion catalyst, an NO—$NO_2$ conversion catalyst, an oxidation catalyst, a soot filter, and/or a reductant injector. In certain embodiments, the functional performance description includes a catalyst conversion efficiency value, a catalyst storage capacity value, a filter integrity value, and/or an injection compliance value.

In certain embodiments, the component performance description includes a functional performance description of a model, and the performance feedback module further adjusts an engine operating parameter by modifying the model. The model includes an engine-out soot model, an engine-out NOx model, an engine-out NOx composition model, a NOx adsorption model, a NOx release model, a NOx conversion model, a hydrocarbon oxidation model, an ammonia slip model, an unburned hydrocarbon slip model, and/or a urea hydrolysis model. The exhaust gas constituent includes an amount of ammonia and an amount of $NO_x$, where the component performance description includes an ammonia: NOx ratio, and the engine operating parameter includes a urea injection rate.

Another exemplary embodiment is a method including providing an exhaust stream for an internal combustion engine, the exhaust stream fluidly coupled to an aftertreatment component, optically determining an amount of an exhaust gas constituent in the exhaust stream, and modifying a model stored on a computer readable medium in response to the amount of the exhaust gas constituent. The modifying the model includes calibrating a modeling parameter, resetting a modeling parameter, and/or resetting an integrator. In an exemplary embodiment, the exhaust gas constituent includes soot, and modifying the model includes calibrating an engine soot generation model.

In certain embodiments, the exhaust gas constituent includes $NO_x$, and modifying the model includes calibrating an engine $NO_x$ generation model, modifying a catalyst $NO_x$ storage model, modifying a catalyst $NO_x$ conversion model, and modifying a catalyst NO to $NO_2$ conversion model. In certain embodiments, the exhaust gas constituent includes urea, and the method further includes determining the exhaust gas constituent at a number of spatially divided portions of the exhaust stream. Modifying the model further includes modifying a urea hydrolysis model.

While the invention has been illustrated and described in detail in the drawings and foregoing description, the same is to be considered as illustrative and not restrictive in character, it being understood that only certain illustrative embodiments have been shown and described and that all changes and modifications that come within the spirit of the inventions are desired to be protected. It should be understood that any relative characterization of embodiments such as but not limited to preferable, preferably, preferred, more preferred, advantageous, or exemplary utilized in the description above indicate that the embodiments or features thereof so described may be more desirable or characteristic, nonetheless the embodiments or features thereof may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method comprising:
providing an exhaust stream for an internal combustion engine, the exhaust stream fluidly coupled to an aftertreatment component;
optically determining an amount of an exhaust gas constituent in the exhaust stream during the operation of the internal combustion engine; and
modifying a model stored on a computer readable medium in response to the amount of the exhaust gas constituent, wherein the modifying the model comprises at least one modifying action selected from the modifying actions consisting of calibrating a modeling parameter, resetting a modeling parameter, and resetting an integrator.

2. The method of claim 1, wherein the exhaust gas constituent comprises soot, and wherein the modifying the model comprises calibrating an engine soot generation model.

3. The method of claim 1, wherein the exhaust gas constituent comprises $NO_x$, and wherein the modifying the model comprises at least one modifying action selected from the modifying actions consisting of calibrating an engine $NO_x$ generation model, modifying a catalyst $NO_x$ storage model, modifying a catalyst $NO_x$ conversion model, and modifying a catalyst NO to $NO_2$ conversion model.

4. The method of claim 1, wherein the exhaust gas constituent comprises urea, the method further comprising determining the exhaust gas constituent at a plurality of spatially divided portions of the exhaust stream, and wherein the modifying the model comprises modifying a urea hydrolysis model.

5. The method of claim 1, wherein the exhaust gas constituent comprises $NO_x$, and wherein the modifying the model comprises modifying a $NO_x$ release model.

6. The method of claim 1, wherein the modifying the model comprises modifying a hydrocarbon slip model.

7. The method of claim 1, wherein the modifying the model comprises modifying an unburned hydrocarbons model.

8. The method of claim 1, wherein the exhaust gas constituent comprises ammonia, and wherein the modifying the model comprises modifying an ammonia slip model.

9. The method of claim 1, wherein the exhaust gas constituent comprises $NO_x$, and wherein the modifying the model comprises calibrating an engine $NO_x$ generation model.

10. The method of claim 1, wherein the exhaust gas constituent comprises $NO_x$, and wherein the modifying the model comprises modifying a catalyst $NO_x$ storage model.

11. The method of claim 1, wherein the exhaust gas constituent comprises $NO_x$, and wherein the modifying the model comprises modifying a catalyst $NO_x$ conversion model.

12. The method of claim 1, wherein the exhaust gas constituent comprises $NO_x$, and wherein the modifying the model comprises modifying a catalyst NO to $NO_2$ conversion model.

* * * * *